US010815534B2

(12) United States Patent
Dudenkov et al.

(10) Patent No.: US 10,815,534 B2
(45) Date of Patent: Oct. 27, 2020

(54) METHODS AND MATERIALS FOR TREATING ESTROGEN RECEPTOR POSITIVE BREAST CANCER

(71) Applicant: Mayo Foundation for Medical Education and Research, Rochester, MA (US)

(72) Inventors: Tanda T. Dudenkov, Rochester, MN (US); Liewei Wang, Rochester, MN (US); James N. Ingle, Rochester, MN (US); Richard M. Weinshilboum, Rochester, MN (US); Junmei Cairns, Altura, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 16/327,671

(22) PCT Filed: Aug. 22, 2017

(86) PCT No.: PCT/US2017/047937
§ 371 (c)(1),
(2) Date: Feb. 22, 2019

(87) PCT Pub. No.: WO2018/039185
PCT Pub. Date: Mar. 1, 2018

(65) Prior Publication Data
US 2019/0194761 A1 Jun. 27, 2019

Related U.S. Application Data

(60) Provisional application No. 62/378,569, filed on Aug. 23, 2016.

(51) Int. Cl.
*C12Q 1/6886* (2018.01)
*G01N 33/50* (2006.01)

(52) U.S. Cl.
CPC ............ *C12Q 1/6886* (2013.01); *G01N 33/50* (2013.01); *C12Q 2600/106* (2013.01); *C12Q 2600/156* (2013.01)

(58) Field of Classification Search
CPC ............ C12Q 1/6886; C12Q 2600/156; C12Q 2600/106
See application file for complete search history.

(56) References Cited

U.S. PATENT DOCUMENTS

| 8,911,937 | B2 | 12/2014 | Wojdacz et al. |
| 2004/0192598 | A1 | 9/2004 | Kragie |
| 2009/0246789 | A1 | 10/2009 | Buckhaults et al. |
| 2013/0209473 | A1* | 8/2013 | de Sauvage ..... A61K 39/39558 424/139.1 |
| 2015/0252409 | A1 | 9/2015 | Scott et al. |
| 2016/0051597 | A1 | 2/2016 | Saha et al. |

FOREIGN PATENT DOCUMENTS

WO   WO 2015/164432   10/2015

OTHER PUBLICATIONS

Anderson et al., "Effects of conjugated equine estrogen in postmenopausal women with hysterectomy: the Women's Health Initiative randomized controlled trial," JAMA., 291(14):1701-12, Apr. 2004.
Carter et al., "Diethylstilbestrol: recommended dosages for different categories of breast cancer patients. Report of the Cooperative Breast Cancer Group," JAMA., 237(19):2079-8, May 1977.
Ellis et al., "Lower-dose vs high-dose oral estradiol therapy of hormone receptor-positive, aromatase inhibitor-resistant advanced breast cancer: a phase 2 randomized study," JAMA., 302(7):774-80, Aug. 2009.
Haddow et al., "Influence of Synthetic Oestrogens on Advanced Malignant Disease," Br. Med. J., 2(4368):393-398, Sep. 1944.
International Search Report in International Application No. PCT/US2017/047937 dated Nov. 6, 2017, 2 pages.
Kamal et al., "Loss of CSMD1 expression is associated with high tumour grade and poor survival in invasive ductal breast carcinoma," Breast Cancer Res. Treat., 121(3):555-63, Jun. 2010.
Kuusisto et al., "Copy Number Variation Analysis in Familial BRCA 1/2-Negative Finnish Breast and Ovarian Cancer," PLos One, 8(8):e71802, Aug. 2013.
Ma et al., "Characterization CSMD1 in a large set of primary lung, head and neck, breast and skin cancer tissues," Cancer Biol Ther., 8(10):907-16, May 2009.
Madhavan et al., "ERRγ target genes are poor prognostic factors in Tamoxifen-treated breast cancer," Journal of Experimental & Clinical Cancer Research, 34(1):45, Dec. 2015.
Nabholtz et al., "Anastrozole is superior to tamoxifen as first-line therapy for advanced breast cancer in postmenopausal women: results of a North American multicenter randomized trial. Arimidex Study Group," Journal of Clinical Oncology, 18(22):3758-3767, Nov. 2000.
Song et al., "Effect of long-term estrogen deprivation on apoptotic responses of breast cancer cells to 17beta-estmdiol," J. Natl. Cancer Inst., 93(22):1714-23, Nov. 2001.

(Continued)

*Primary Examiner* — Jeffrey S Lundgren
*Assistant Examiner* — Michael J Schmitt
(74) *Attorney, Agent, or Firm* — Fish & Richardson P.C.

(57) ABSTRACT

This document provides methods and materials for treating cancer (e.g., estrogen receptor positive breast cancer). For example, methods and materials for identifying a mammal (e.g., a human) with cancer (e.g., estrogen receptor positive breast cancer) as having A→G variant genotype of rs6990851 and/or as having an elevated level of CSMD1 nucleic acid expression and administering one or more aromatase inhibitors (e.g., anastrozole) to treat the mammal identified as having such genotype and/or elevated level are provided.

10 Claims, 7 Drawing Sheets

(56) References Cited

OTHER PUBLICATIONS

Stoll et al., "Hypothesis: breast cancer regression under oestrogen therapy," Br. Med. J., 3(5877):446-50, Aug. 1973.
Written Opinion of the International Searching Authority in International Application No. PCT/US2017/047937 dated Nov. 6, 2017, 7 pages.

* cited by examiner

METHODS AND MATERIALS FOR TREATING ESTROGEN RECEPTOR POSITIVE BREAST CANCER

CROSS-REFERENCE TO RELATED APPLICATIONS

This application is a National Stage application under 35 U.S.C. § 371 of International Application No. PCT/US2017/047937, having an International Filing Date of Aug. 22, 2017, which claims priority to U.S. Application Ser. No. 62/378,569, filed on Aug. 23, 2016. The disclosures of the prior applications are considered part of (and are incorporated by reference in) the disclosure of this application.

BACKGROUND

1. Technical Field

This document relates to methods and materials involved in treating cancer (e.g., estrogen receptor positive breast cancer). For example, this document provides methods and materials for identifying estrogen receptor positive breast cancer patients who are responsive to an aromatase inhibitor (e.g., anastrozole). This document also provides methods and materials for treating estrogen receptor positive breast cancer patients identified as being responsive to an aromatase inhibitor (e.g., anastrozole) with an aromatase inhibitor (e.g., anastrozole).

2. Background Information 70-80 percent of all breast cancer patients are estrogen receptor alpha (ERα) positive. The mainstream treatment of ERα positive breast cancer involves hormonal therapy, which includes the use of tamoxifen to block the action of estrogen and/or the use of aromatase inhibitors to inhibit estrogen synthesis.

SUMMARY

This document provides methods and materials for treating cancer (e.g., estrogen receptor positive breast cancer). For example, this document provides methods and materials for identifying a mammal (e.g., a human) with cancer (e.g., estrogen receptor positive breast cancer) as having an A→G variant genotype of rs6990851 and/or as having an elevated level of CSMD1 nucleic acid expression and administering one or more aromatase inhibitors (e.g., anastrozole) to treat the mammal identified as having such genotype and/or elevated level. As described herein, estrogen receptor positive breast cancer patients identified as having an A→G variant genotype of rs6990851 and/or as having an elevated level of CSMD1 nucleic acid expression can be more responsive to treatment with an aromatase inhibitor (e.g., anastrozole) than patients lacking such genotype and elevated expression level.

This document also provides methods and materials for identifying a mammal as having a cancer (e.g., estrogen receptor positive breast cancer) that is responsive to treatment with one or more aromatase inhibitors (e.g., anastrozole). For example, mammals (e.g., humans) having estrogen receptor positive breast cancer can be assessed to determine if they have an A→G variant genotype of rs6990851 and/or an elevated level of CSMD1 nucleic acid expression. If the mammal has an A→G variant genotype of rs6990851 and/or an elevated level of CSMD1 nucleic acid expression, then the mammal can be classified as having a cancer responsive to treatment with one or more aromatase inhibitors (e.g., anastrozole). If the mammal does not have an A→G variant genotype of rs6990851 and does not have an elevated level of CSMD1 nucleic acid expression, then the mammal can be classified as having a cancer that is less responsive to treatment with an aromatase inhibitor (e.g., anastrozole).

In general, one aspect of this document features a method for treating cancer in a mammal. The method comprises, or consists essentially of, (a) identifying the mammal as having an A→G variant genotype of rs6990851 or an elevated level of CSMD1 nucleic acid expression, and (b) administering an aromatase inhibitor to the mammal under conditions wherein the length of time the mammal remains free of an adverse cancer event is lengthened as compared to the length of time a comparable mammal lacking the A→G variant genotype of rs6990851 and lacking the elevated level remains free of an adverse cancer event. The mammal can be a human. The cancer can be estrogen receptor positive breast cancer. The method can comprise identifying the mammal as having the A→G variant genotype of rs6990851. The method can comprise identifying the mammal as being heterozygous for the A→G variant genotype of rs6990851. The method can comprise identifying the mammal as being homozygous for the A→G variant genotype of rs6990851. The method can comprise identifying the mammal as having the elevated level. The aromatase inhibitor can be anastrozole.

In another aspect, this document features a method for identifying a mammal with cancer as being responsive to treatment with an aromatase inhibitor. The method comprises, or consists essentially of, (a) determining that the mammal has an A→G variant genotype of rs6990851 or an elevated level of CSMD1 nucleic acid expression, and (b) classifying the mammal as having cancer susceptible to treatment with the aromatase inhibitor. The mammal can be a human. The cancer can be estrogen receptor positive breast cancer. The method can comprise determining the mammal has the A→G variant genotype of rs6990851. The method can comprise determining the mammal is heterozygous for the A→G variant genotype of rs6990851. The method can comprise determining the mammal is homozygous for the A→G variant genotype of rs6990851. The method can comprise determining the mammal has the elevated level. The aromatase inhibitor can be anastrozole.

In another aspect, this document features a method for treating cancer in a mammal. The method comprises, or consists essentially of, administering an aromatase inhibitor to the mammal and administering estradiol to the mammal. The mammal can be a human. The cancer can be estrogen receptor positive breast cancer. The method can comprise identifying the mammal as having an A→G variant genotype of rs6990851. The method can comprise identifying the mammal as being heterozygous for an A→G variant genotype of rs6990851. The method can comprise identifying the mammal as being homozygous for an A→G variant genotype of rs6990851. The method can comprise identifying the mammal as having an elevated level of CSMD1 nucleic acid expression. The aromatase inhibitor can be anastrozole.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

Figures 1A, 1B:
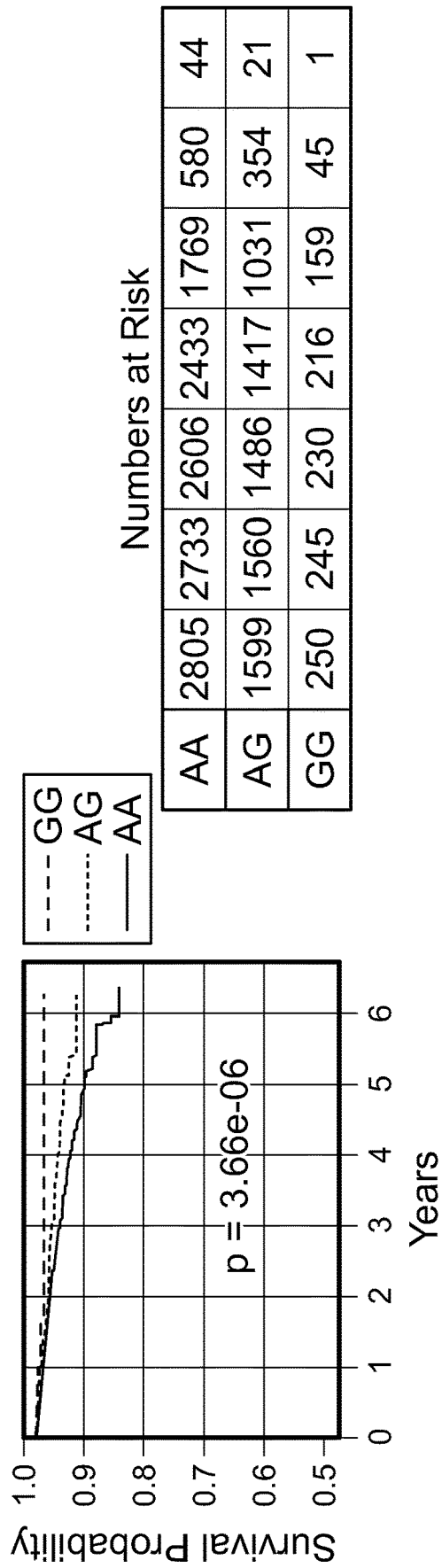
FIG. 1A contains a graph plotting Kaplan-Meier curves for time to breast cancer event by rs69900851 genotype.
FIG. 1B is a table containing SNP association results for time to distant metastasis.

This document provides methods and materials for treating cancer (e.g., estrogen receptor positive breast cancer). For example, this document provides methods and materials for identifying a mammal (e.g., a human) with cancer (e.g., estrogen receptor positive breast cancer) as having an A→G variant genotype of rs6990851 and/or as having an elevated level of CSMD1 nucleic acid expression and administering one or more aromatase inhibitors (e.g., anastrozole) to treat the mammal identified as having such genotype and/or elevated level. Any appropriate mammal having cancer (e.g., estrogen receptor positive breast cancer) can be treated as described herein. For example, humans and other primates such as monkeys having cancer (e.g., estrogen receptor positive breast cancer) can be identified as having an A→G variant genotype of rs6990851 and/or as having an elevated level of CSMD1 nucleic acid expression and treated with one or more aromatase inhibitors (e.g., anastrozole) to prolong the time the human or other primate remains free of a cancer event (e.g., a breast cancer event such as local or metastatic breast cancer). In some cases, dogs, cats, horses, cows, pigs, sheep, mice, and rats can be identified and treated with one or more aromatase inhibitors as described herein.

A mammal having any appropriate cancer can be assessed for the presence of an A→G variant genotype of rs6990851 and/or the presence of an elevated level of CSMD1 nucleic acid expression and, if present, treated as described herein. For example, a human having breast cancer (e.g., estrogen receptor positive breast cancer) can be assessed for an A→G variant genotype of rs6990851 (e.g., a homozygous variant genotype (GG) of rs6990851) and/or the presence of an elevated level of CSMD1 nucleic acid expression and treated with one or more aromatase inhibitors as described herein.

Any appropriate method can be used to identify a mammal having cancer (e.g., estrogen receptor positive breast cancer). For example, imaging techniques and biopsy techniques can be used to identify mammals (e.g., humans) having cancer. In some case, immunological techniques such as anti-estrogen receptor cell staining techniques can be used to identify mammals (e.g., humans) having estrogen receptor positive breast cancer.

Once identified as having cancer (e.g., estrogen receptor positive breast cancer), the mammal (e.g., human) can be assessed to determine if the mammal is homozygous for the wild-type genotype (AA) of rs6990851, heterozygous for the variant genotype (AG) of rs6990851, or homozygous for the variant genotype (GG) of rs6990851. For example, a mammal (e.g., a human) identified as having breast cancer and treated with surgery, chemotherapy, or both can be assessed to determine if the mammal is homozygous for the wild-type genotype (AA) of rs6990851, heterozygous for the variant genotype (AG) of rs6990851, or homozygous for the variant genotype (GG) of rs6990851. Any appropriate method can be used to identify the mammal's genotype of rs6990851. For example, genomic DNA from a mammal can be sequenced to determine the mammal's genotype of rs6990851. In some cases, amplification or SNP detection assays can be used to determine the mammal's genotype of rs6990851.

In some cases, the mammal (e.g., human) can be assessed to determine if the mammal expresses an elevated level of CSMD1 nucleic acid. Any appropriate method can be used to determine if the mammal contains cells (e.g., breast tumor cells) that express an elevated level of CSMD1 nucleic acid. For example, mRNA-based assays such as RT-PCR can be used to identify cells as expressing an elevated level of CSMD1 nucleic acid. In some cases, polypeptide-based assays such as antibody staining techniques or ELISAs using anti-CSMD1 polypeptide antibodies can be performed to identify cells as expressing an elevated level of CSMD1 nucleic acid.

The term "elevated level" as used herein with respect to the level of CSMD1 nucleic acid expression can be in comparison with the median CSMD1 nucleic acid expression level present in cells from a random sampling comparable mammals (e.g., humans) known not to have cancer (e.g., the median CSMD1 expression level determined from samples from a random sampling of 5, 10, 15, 20, 30, 40, 50, 100, 500, or more humans known not to have cancer). In some cases, an elevated level of CSMD1 nucleic acid expression can be at least 5, 10, 20, 30, 40, 50, 75, or 100 percent greater than the median CSMD1 nucleic acid expression level present in cells from a random sampling of comparable mammals known not to have cancer.

Once identified as having an A→G variant genotype of rs6990851 (e.g., a heterozygous variant genotype (AG) of rs6990851 or a homozygous variant genotype (GG) of rs6990851) and/or the presence of an elevated level of CSMD1 nucleic acid expression, the mammal can be administered or instructed to self-administer one or more aromatase inhibitors to prolong the time the mammal remains free of a cancer event (e.g., no detectable tumors from imaging and/or pathological analysis). Examples of aromatase inhibitors include, without limitation, anastrozole, letrozole, and exemestane. In some cases, two or more aromatase inhibitors (e.g., two, three, four, five, or more aromatase inhibitors) can be administered to a mammal to prolong the time the mammal remains free of a cancer event (e.g., no detectable tumors from imaging and/or pathological analysis). In some cases, one or more aromatase inhibitors can be administered to a mammal once or multiple times over a period of time ranging from days to weeks. In some cases, one or more aromatase inhibitors can be formulated into a pharmaceutically acceptable composition for administration to a mammal (e.g., a mammal being treated for breast cancer). For example, a therapeutically effective amount of an aromatase inhibitor (e.g., anastrozole) can be formulated together with one or more pharmaceutically acceptable carriers (additives) and/or diluents. A pharmaceutical composition can be formulated for administration in solid or liquid form including, without limitation, sterile solutions, suspensions, sustained-release formulations, tablets, capsules, pills, powders, and granules.

Pharmaceutically acceptable carriers, fillers, and vehicles that can be used in a pharmaceutical composition described herein include, without limitation, ion exchangers, alumina, aluminum stearate, lecithin, serum proteins such as human serum albumin, buffer substances such as phosphates, glycine, sorbic acid, potassium sorbate, partial glyceride mixtures of saturated vegetable fatty acids, water, salts or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol, and wool fat.

A pharmaceutical composition containing one or more aromatase inhibitors can be designed for oral or parenteral (including subcutaneous, intramuscular, intravenous, and intradermal) administration. When being administered orally, a pharmaceutical composition can be in the form of a pill, tablet, or capsule. Compositions suitable for parenteral administration can include aqueous and non-aqueous sterile injection solutions that can contain anti-oxidants, buffers, bacteriostats, and solutes that render the formulation isotonic with the blood of the intended recipient. The formulations can be presented in unit-dose or multi-dose containers, for example, sealed ampules and vials, and may be stored in a freeze dried (lyophilized) condition requiring only the addition of the sterile liquid carrier, for example, water for injections, immediately prior to use. Extemporaneous injection solutions and suspensions may be prepared from sterile powders, granules, and tablets.

Effective doses can vary depending on the severity of the cancer, the route of administration, the age and general health condition of the subject, excipient usage, the possibility of co-usage with other therapeutic treatments such as use of other agents, and the judgment of the treating physician.

An effective amount of a composition containing one or more aromatase inhibitors can be any amount that inhibits aromatase activity within the mammal without producing significant toxicity to the mammal. For example, an effective amount of an aromatase inhibitor such as anastrozole can be from about 0.625 mg/m$^2$ to about 30 mg/m$^2$ (e.g., from about 0.75 mg/m$^2$ to about 30 mg/m$^2$, from about 1.0 mg/m$^2$ to about 30 mg/m$^2$, from about 5 mg/m$^2$ to about 30 mg/m$^2$, from about 10 mg/m$^2$ to about 30 mg/m$^2$, from about 0.625 mg/m$^2$ to about 25 mg/m$^2$, from about 0.625 mg/m$^2$ to about 20 mg/m$^2$, from about 0.625 mg/m$^2$ to about 10 mg/m$^2$, from about 0.75 mg/m$^2$ to about 25 mg/m$^2$, from about 1.0 mg/m$^2$ to about 15 mg/m$^2$, from about 1.5 mg/m$^2$ to about 10 mg/m$^2$, or from about 2 mg/m$^2$ to about 10 mg/m$^2$). In some cases, from about 1 mg to about 10 mg of an aromatase inhibitor such as anastrozole can be administered to an average sized human (e.g., about 75-85 kg human) about daily for about one year to about five years (or for the mammal's lifetime).

The effective amount can remain constant or can be adjusted as a sliding scale or variable dose depending on the mammal's response to treatment. Various factors can influence the actual effective amount used for a particular application. For example, the frequency of administration, duration of treatment, use of multiple treatment agents, route of administration, and severity of the condition (e.g., cancer) may require an increase or decrease in the actual effective amount administered.

The frequency of administration of an aromatase inhibitor can be any amount that maintains a fairly steady state of inhibited aromatase activity within the mammal without producing significant toxicity to the mammal. For example, the frequency of administration of an aromatase inhibitor can be from about twice daily to about once a week. In some cases, the frequency of administration of an aromatase inhibitor can be daily. The frequency of administration of an aromatase inhibitor can remain constant or can be variable during the duration of treatment. A course of treatment with a composition containing an aromatase inhibitor can include rest periods. For example, a composition containing one or more aromatase inhibitors can be administered daily over a two week period followed by a one week rest period, and such a regimen can be repeated multiple times. As with the effective amount, various factors can influence the actual frequency of administration used for a particular application. For example, the effective amount, duration of treatment, use of multiple treatment agents, route of administration, and severity of the condition (e.g., cancer) may require an increase or decrease in administration frequency.

An effective duration for administering a composition containing one or more aromatase inhibitors can be any appropriate duration that does not produce significant toxicity to the mammal. In some cases, the effective duration can vary from several weeks to several years (e.g., 5, 10, 15, or more years). Multiple factors can influence the actual effective duration used for a particular treatment. For example, an effective duration can vary with the frequency of administration, effective amount, use of multiple treatment agents, route of administration, and severity of the condition being treated.

In certain instances, a course of treatment, the level of circulating aromatase inhibitors within a mammal, and/or the presence or absence of adverse cancer events (e.g., osteoporosis and musculoskeletal toxicity) can be monitored. Any appropriate method can be used to determine whether or not adverse cancer events occurred. For example, imaging techniques can be used to assess the mammal's tissue for the presence or absence of metastatic breast cancer.

In some cases, a mammal having cancer (e.g., estrogen receptor positive breast cancer) can be treated with one or more aromatase inhibitors (e.g., one, two, three, four, five, or more aromatase inhibitors) and estradiol to prolong the time the mammal remains free of a cancer event (e.g., no detectable tumors from the imaging or pathological analysis). For example, a mammal (e.g., a human) having estrogen receptor positive breast cancer can be administered an effective amount of an aromatase inhibitor (e.g., anastrozole) as described herein and an effective amount of estradiol. An effective amount of estradiol can be from about 3.75 mg/m$^2$ to about 18.75 mg/m$^2$ (e.g., from about 4 mg/m$^2$ to about 18.75 mg/m$^2$, from about 5 mg/m$^2$ to about 18.75 mg/m$^2$, from about 7.5 mg/m$^2$ to about 18.75 mg/m$^2$, from about 10 mg/m$^2$ to about 18.75 mg/m$^2$, from about 3.75 mg/m$^2$ to about 15 mg/m$^2$, from about 3.75 mg/m$^2$ to about 12 mg/m$^2$, from about 3.75 mg/m$^2$ to about 10 mg/m$^2$, from about 3.75 mg/m$^2$ to about 7.5 mg/m$^2$, from about 4 mg/m$^2$ to about 15 mg/m$^2$, or from about 5 mg/m$^2$ to about 15 mg/m$^2$). In some cases, from about 6 mg to about 30 mg of estradiol can be administered to an average sized human (e.g., about 75-85 kg human) daily for about three months to about four years (or for the mammal's lifetime). In some cases, 2 mg or 10 md of estradiol can be administered three times a day.

The invention will be further described in the following examples, which do not limit the scope of the invention described in the claims.

EXAMPLES

Figure 2:
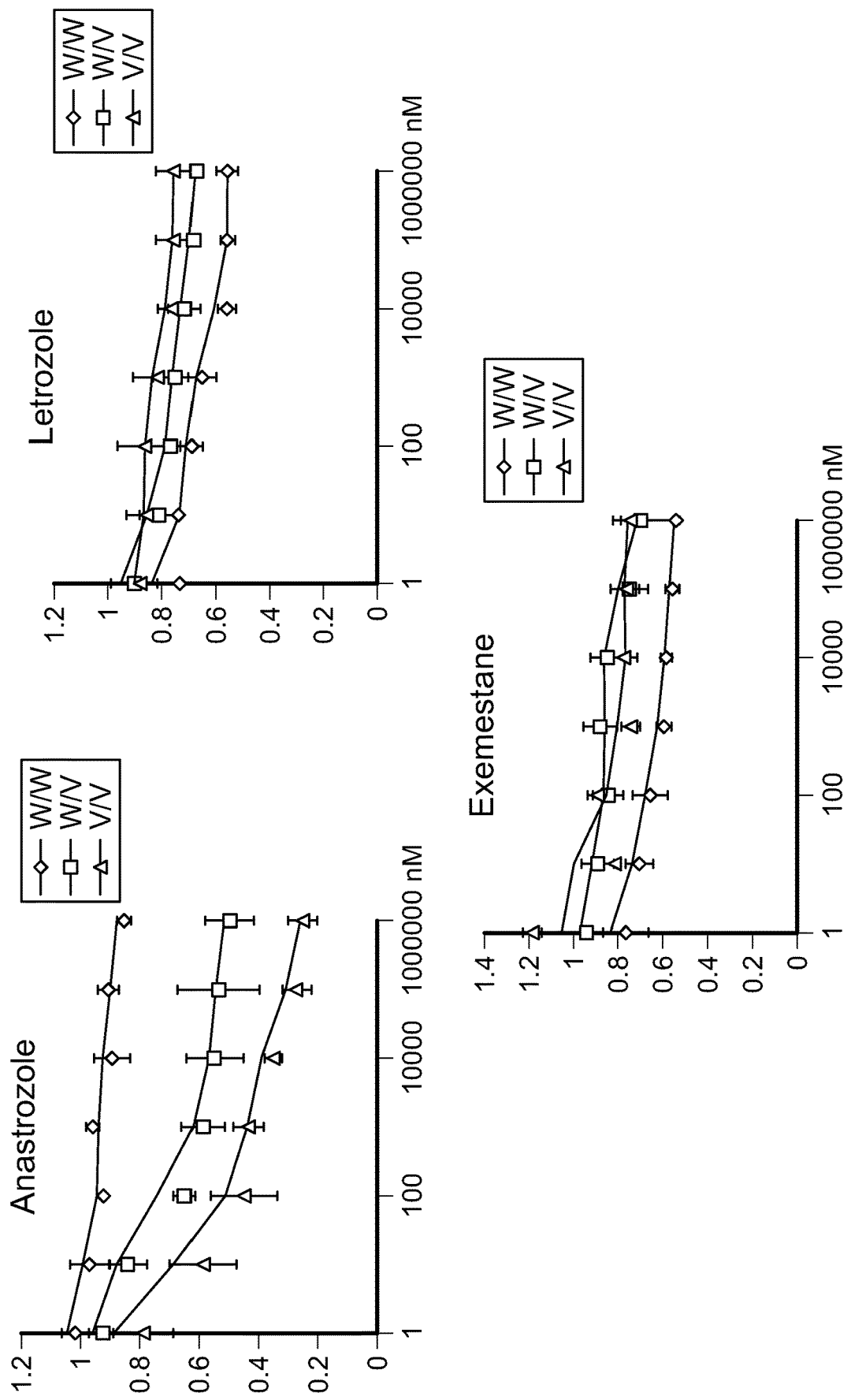
FIG. 2 contains graphs plotting the sensitivity of human lymphoblastoid cell lines (homozygous WT rs6990851 genotype (AA), heterozygous rs6990851 genotype (AG), and homozygous variant rs6990851 genotype (GG)) to exposure to the indicated amounts of anastrozole, letrozole, or exemestane.
Figure 3:
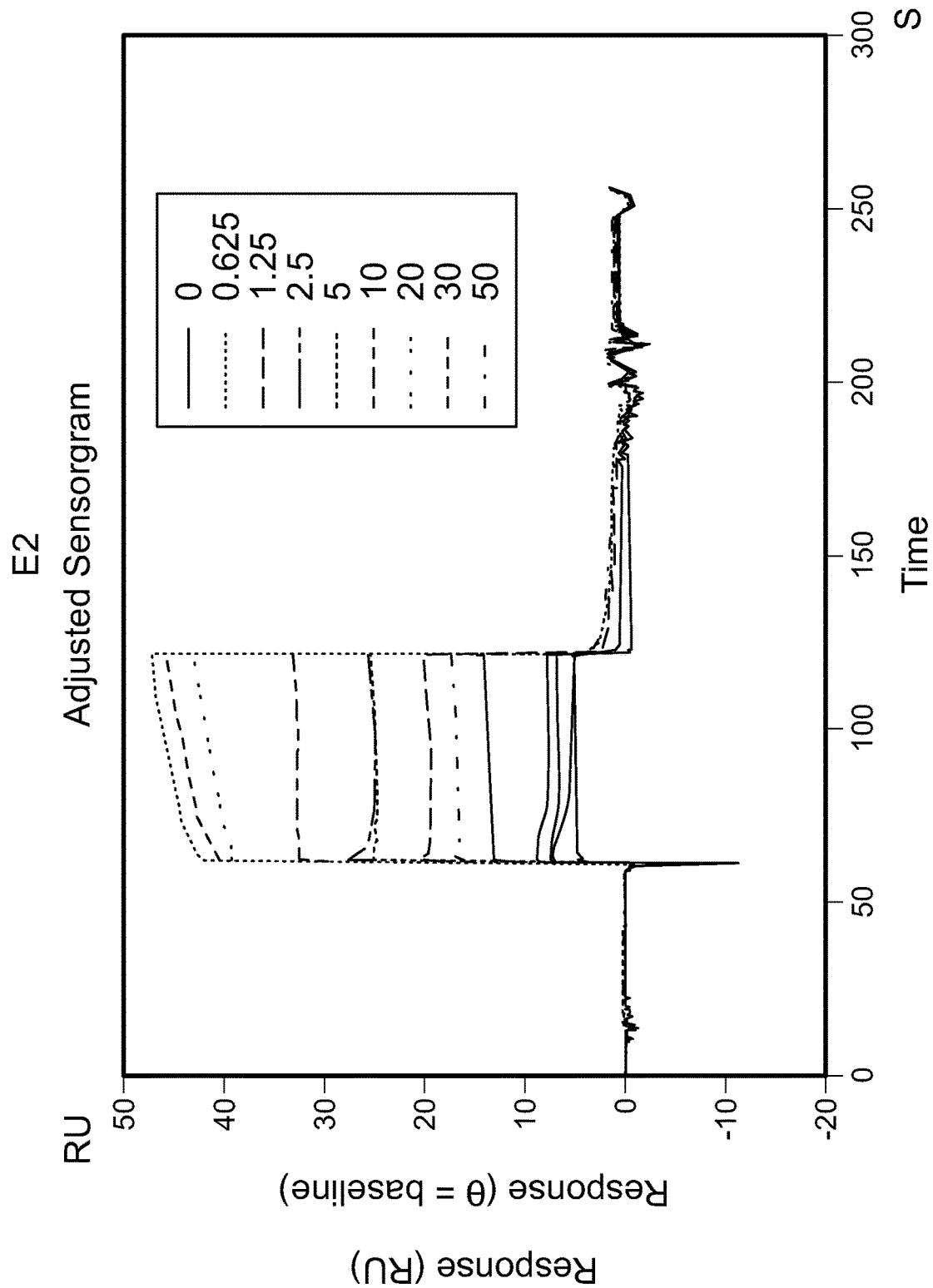
FIG. 3 is graph plotting adjusted sensograms for direct binding between the indicated amounts (0, 0.625, 1.25, 2.5, 5, 10, 20, 30, and 50 μM) of E2 and ERα using a surface plasmon resonance (SPR) method.

Example 1—Identifying Cancer Patients Responsive to Treatment with Aromatase Inhibitors to Prolong the Time the Patients Remain Free of a Cancer Event A genome wide association study was performed, and the SNP rs6990851 (GG variant genotype) in the CSMD1 was identified as being associated with significantly increased time to breast events as shown in the Kaplan-Meier Curve (FIG. 1). The protective effect of the GG variant genotype of rs6990851 was observed in patients with distant metastasis, a manifestation of 60-70 percent of all patients with breast events and treated with anastrozole (FIG. 1B). Patients with homozygous GG variant SNPs exhibited increased CSMD1 and aromatase gene expression which in turn, sensitized cells to anastrozole, but not to letrozole and exemestane. This was further confirmed with studies using the cell lines. In human lymphoblastoid cells selected based on the rs6990851 genotype including homozygous WT genotype (AA), heterozygous genotype (AG), and homozygous variant genotype (GG), the homozygous GG variant cells were more sensitive to anastrozole treatment (FIG. 2). This phenomenon was not observed for letrozole and exemestane.

Figure 4:
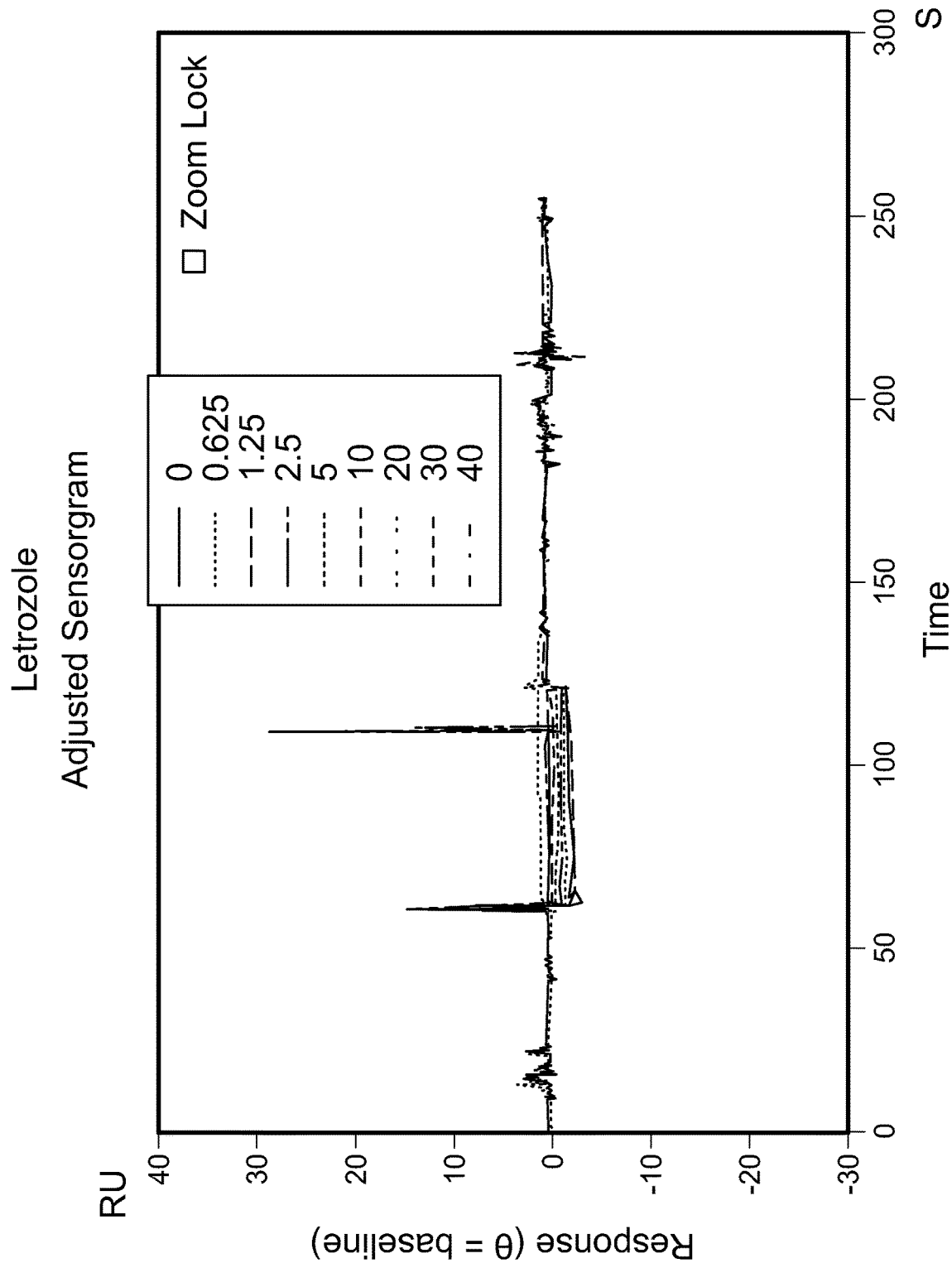
FIG. 4 is graph plotting adjusted sensograms for direct binding between the indicated amounts (0, 0.625, 1.25, 2.5, 5, 10, 20, 30, and 40 μM) of letrozole and ERα using an SPR method.
Figure 5:
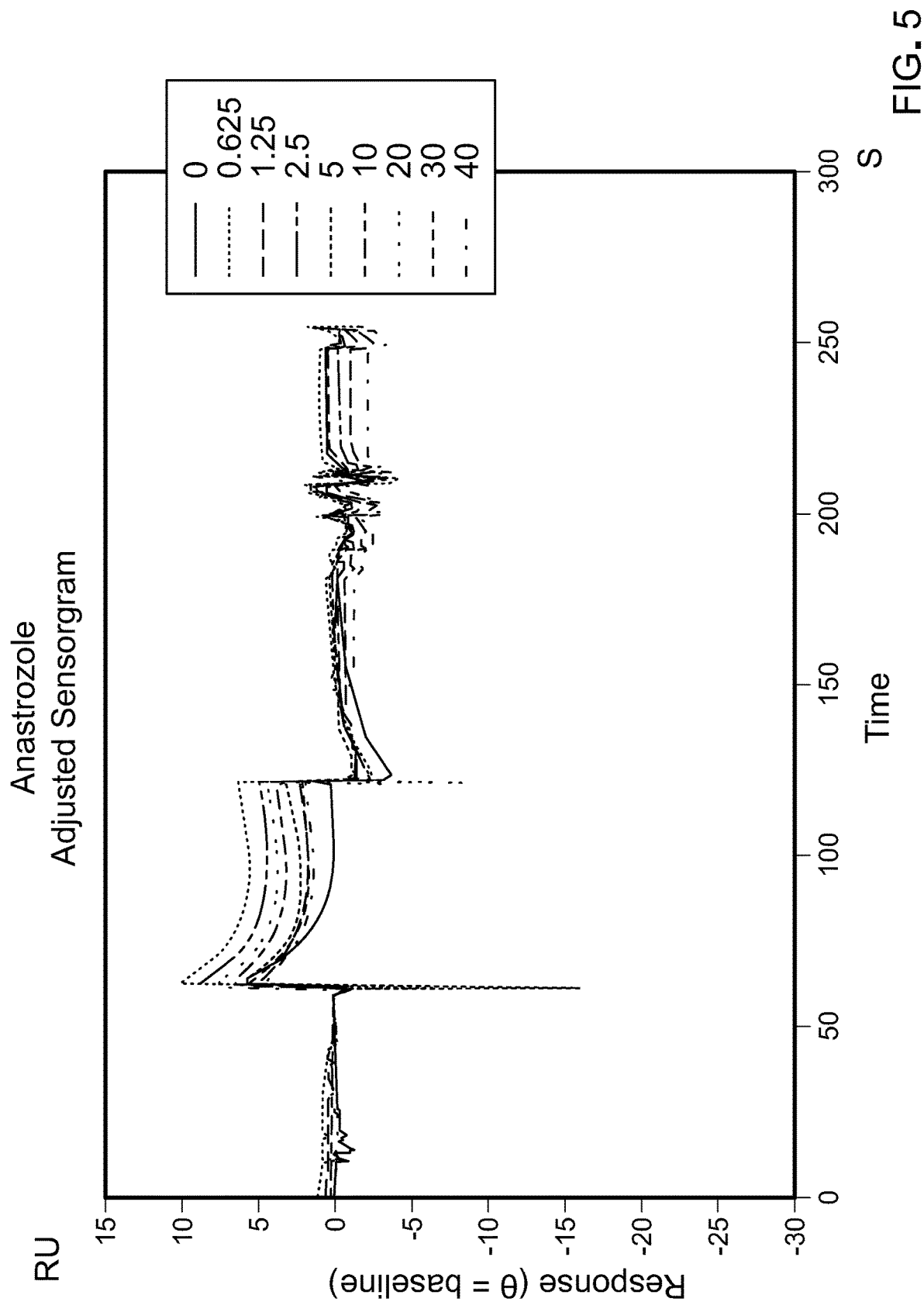
FIG. 5 is graph plotting adjusted sensograms for direct binding between the indicated amounts (0, 0.625, 1.25, 2.5, 5, 10, 20, 30, and 40 μM) of anastrozole and ERα using an SPR method.
Figure 6:
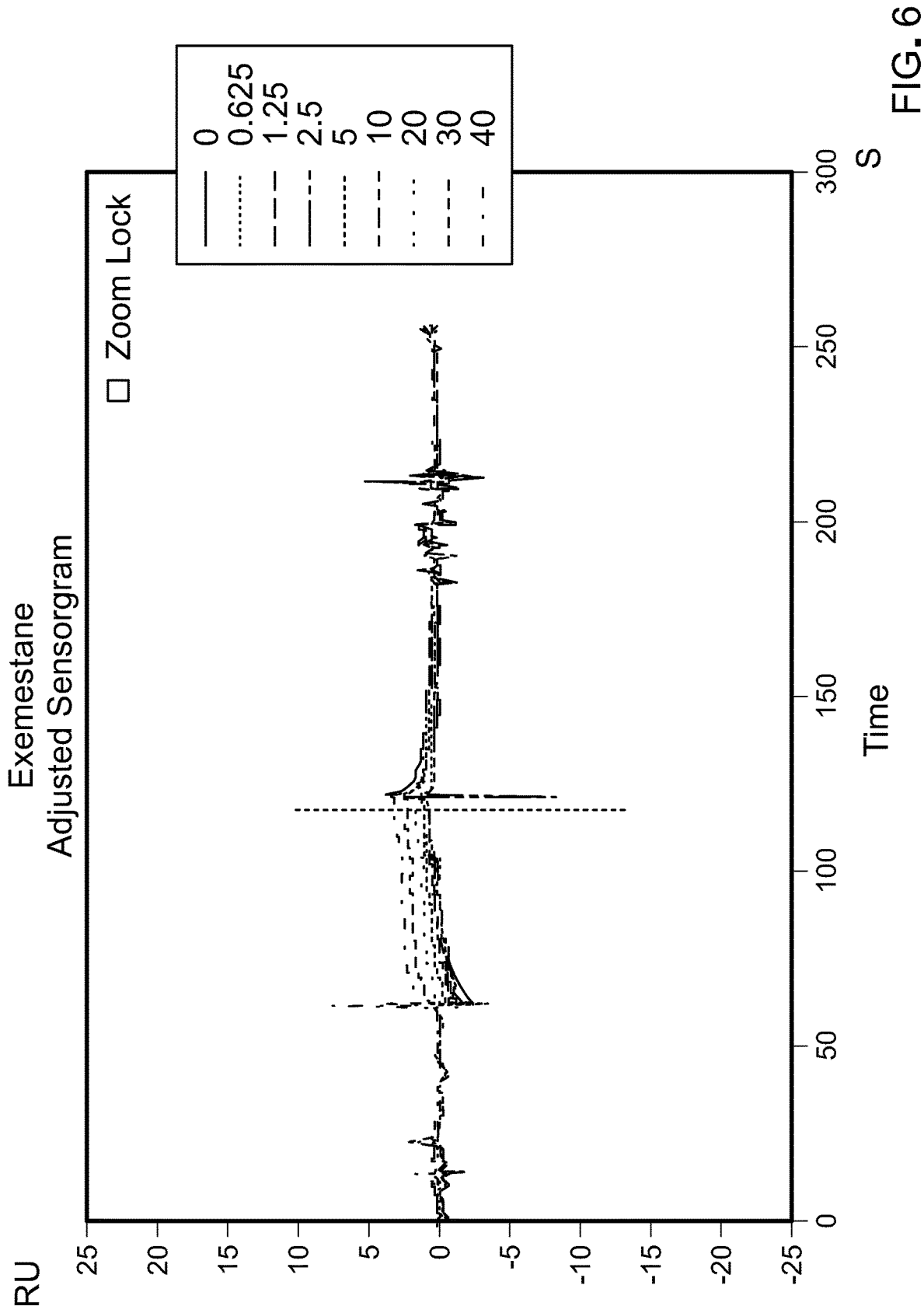
FIG. 6 is graph plotting adjusted sensograms for direct binding between the indicated amounts (0, 0.625, 1.25, 2.5, 5, 10, 20, 30, and 40 μM) of exemestane and ERα using an SPR method.
Figure 7:
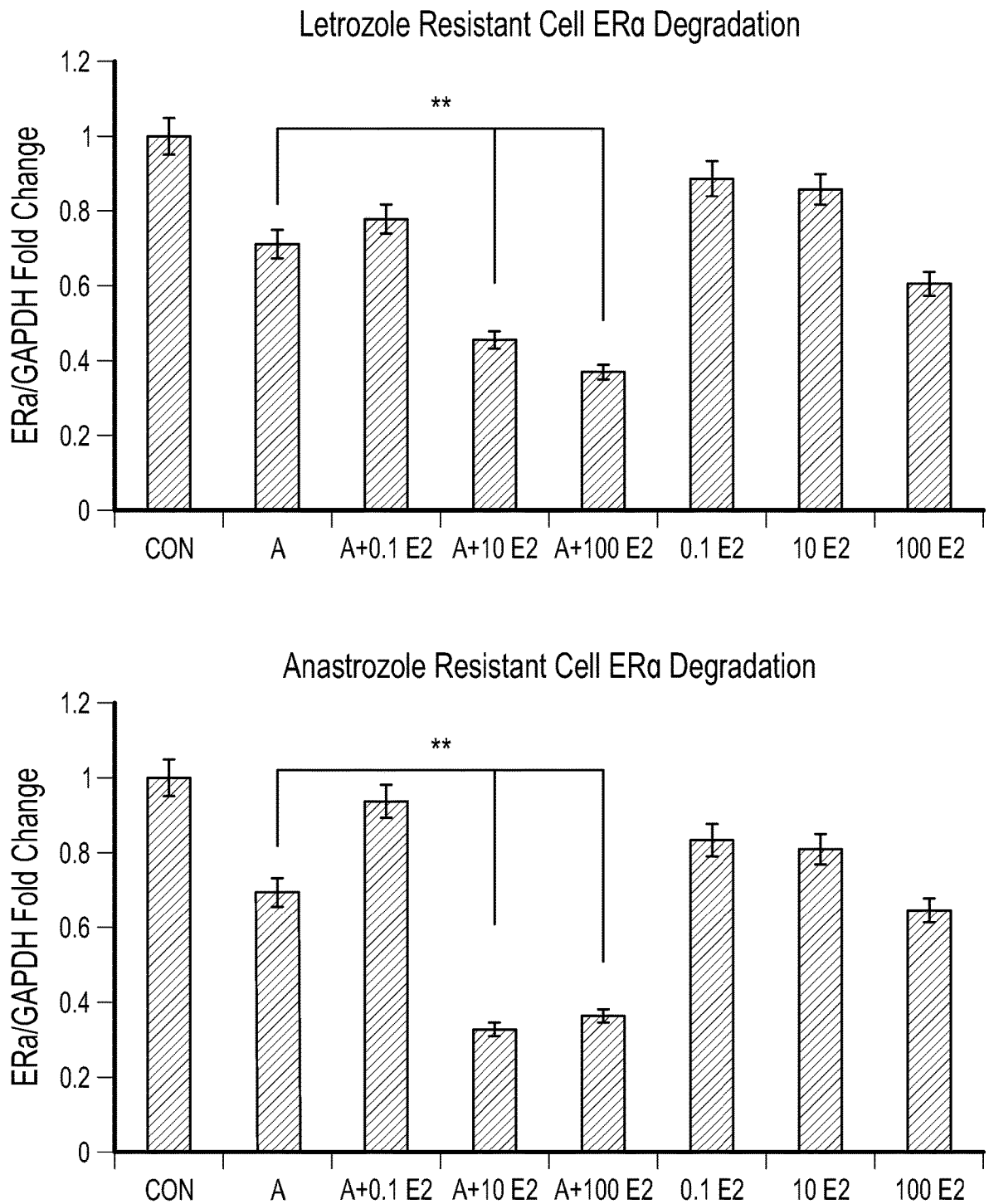
FIG. 7 contains bar graphs plotting the ERα/GADPH fold change (ERα degradation) for letrozole resistant cells (top) or anastrozole resistant cells (bottom).

The difference among the three aromatase inhibitors also was confirmed with in depth mechanistic studies. Overexpression of CSMD1 sensitized ERα$^+$ breast cancer cells to anastrozole. Furthermore, overexpression of CSMD1 sensitized letrozole resistant cells to anastrozole, but not to the other two aromatase inhibitors (i.e., letrozole and exemestane). Cells with the GG variant SNPs were more sensitive only to anastrozole, which was due to the fact that the GG variant SNP increased CSMD1 and aromatase gene expression levels. At a mechanistic level, anastrozole, but not letrozole or exemestane, was found to bind ERα (FIGS. 3-6) and to degrade ERα (FIG. 7). The direct binding between three aromatase inhibitors and ERα was assessed using a surface plasmon resonance (SPR) method (FIGS. 3-6). This method allowed real time label free detection of biomolecular interactions. The traces above the background revealed the positive interaction between anastrozole and ERα (FIG. 5). No interactions were observed based on the SPR data for letrozole and exemestane (FIGS. 4 and 6).

The degradation effect was more significant in the presence of E2 (FIG. 7). The quantitative protein levels were measured by Western blot of ERα in both letrozole and anastrozole resistant cell lines following various treatments including anastrozole (A), anastrozole plus 0.1 nM (A+0.1 E2), 10 nM (A+10 E2), or 100 nM (A+100 E2) of E2, or 0.1 nM (0.1 E2), 10 nM (10 E2), or 100 nM (100 E2) of E2 alone. The combination treatments exhibited significant reduction of ERα protein levels in both resistant cells (FIG. 7).

The results provided herein demonstrate that the GG variant genotype of rs6990851 and/or elevated CSMD1 nucleic acid expression can be used to identify or select patients most appropriate for anastrozole treatment. These results also demonstrate that anastrozole has a novel function besides its effect on inhibition of aromatase activity by binding and degrading ERα, which could be another mechanism for a selected population who might benefit most from anastrozole, but not the other two aromatase inhibitors. Further, these results demonstrate that patients who developed resistance to an aromatase inhibitor treatment can be treated with a combination of E2 and anastrozole.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for treating estrogen receptor positive breast cancer in a mammal, wherein said method comprises:
   (a) identifying said mammal as having an A→G variant genotype of rs6990851 or an elevated level of CSMD1 nucleic acid expression, and
   (b) administering anastrozole to said mammal and administering estradiol (E2) to said mammal.

2. The method of claim 1, wherein said mammal is a human.

3. The method of claim 1, wherein said method comprises identifying said mammal as being heterozygous for an A→G variant genotype of rs6990851.

4. The method of claim 1, wherein said method comprises identifying said mammal as being homozygous for an A→G variant genotype of rs6990851.

5. The method of claim 1, wherein said method comprises identifying said mammal as having an elevated level of CSMD1 nucleic acid expression.

6. A method for treating estrogen receptor positive breast cancer, wherein said method comprises administering anastrozole and estradiol (E2) to a mammal identified as having an A→G variant genotype of rs6990851 or an elevated level of CSMD1 nucleic acid expression.

7. The method of claim 6, wherein said mammal is a human.

8. The method of claim 6, wherein said mammal was identified as being heterozygous for an A→G variant genotype of rs6990851.

9. The method of claim 6, wherein said mammal was identified as being homozygous for an A→G variant genotype of rs6990851.

10. The method of claim 6, wherein said mammal was identified as having an elevated level of CSMD1 nucleic acid expression.

\* \* \* \* \*